US012708593B2

(12) United States Patent
Advani et al.

(10) Patent No.: US 12,708,593 B2
(45) Date of Patent: Aug. 18, 2026

(54) FACE CLEANSER BEADS

(71) Applicant: Seadrop Skincare, New York, NY (US)

(72) Inventors: Serena Advani, New York, NY (US); Monica Advani, Secaucus, NJ (US)

(73) Assignee: Seadrop Skincare, New York, NY (US)

(*) Notice: Subject to any disclaimer, the term of this patent is extended or adjusted under 35 U.S.C. 154(b) by 272 days.

(21) Appl. No.: 18/676,572

(22) Filed: May 29, 2024

(65) Prior Publication Data

US 2024/0398672 A1 Dec. 5, 2024

Related U.S. Application Data

(60) Provisional application No. 63/505,260, filed on May 31, 2023.

(51) Int. Cl.

| | |
|---|---|
| ***A61K 8/00*** | (2006.01) |
| ***A61K 8/02*** | (2006.01) |
| ***A61K 8/26*** | (2006.01) |
| ***A61K 8/66*** | (2006.01) |
| ***A61K 8/73*** | (2006.01) |
| ***A61K 8/92*** | (2006.01) |
| ***A61K 8/9794*** | (2017.01) |
| ***A61Q 19/10*** | (2006.01) |

(52) U.S. Cl.

CPC ................ *A61K 8/022* (2013.01); *A61K 8/26* (2013.01); *A61K 8/66* (2013.01); *A61K 8/732* (2013.01); *A61K 8/735* (2013.01); *A61K 8/922* (2013.01); *A61K 8/9794* (2017.08); *A61Q 19/10* (2013.01)

(58) Field of Classification Search

None

See application file for complete search history.

(56) References Cited

U.S. PATENT DOCUMENTS

| | | | | |
|---|---|---|---|---|
| 4,751,075 | A | 6/1988 | Chernowsky et al. | |
| 5,137,714 | A | 8/1992 | Scott | |
| 5,527,488 | A | 6/1996 | Groh | |
| 7,338,671 | B2 * | 3/2008 | Golz-Berner | A61K 8/26 424/725 |
| 8,361,516 | B2 | 1/2013 | Lintner et al. | |
| 10,029,013 | B2 | 7/2018 | Tamarkin et al. | |
| 10,323,215 | B2 | 6/2019 | Fuchs et al. | |
| 10,610,477 | B2 | 4/2020 | Terrisse et al. | |
| 10,993,891 | B2 | 5/2021 | Mathonneau et al. | |
| 11,261,409 | B2 | 3/2022 | Naqvi | |
| 2003/0211062 | A1 | 11/2003 | Laden et al. | |
| 2004/0228892 | A1 | 11/2004 | Berry et al. | |
| 2007/0184995 | A1 | 8/2007 | Shah et al. | |
| 2009/0286866 | A1 | 11/2009 | Segura-Orsoni et al. | |
| 2015/0037264 | A1 | 2/2015 | Bellamy | |
| 2016/0287484 | A1 * | 10/2016 | Neame | A61K 8/022 |
| 2020/0140781 | A1 | 5/2020 | Harper et al. | |
| 2023/0000753 | A1 | 1/2023 | Macary et al. | |

FOREIGN PATENT DOCUMENTS

| | | | |
|---|---|---|---|
| AU | 2008250484 | B2 | 7/2013 |
| AU | 2009265228 | B2 | 9/2013 |
| AU | 2020225452 | B2 | 12/2022 |
| BR | 112018015897 | B1 | 3/2022 |
| CN | 110868997 | A | 3/2020 |
| EP | 2181694 | A1 | 5/2010 |
| FR | 2873033 | A1 | 1/2006 |
| FR | 3117029 | A1 | 6/2022 |
| FR | 3117030 | A1 | 6/2022 |
| JP | 2009-215256 | A | 9/2009 |
| JP | 2011-148722 | A | 8/2011 |
| JP | 6177634 | B2 | 8/2017 |
| KR | 10-2004-0078598 | A | 9/2004 |
| KR | 10-1114614 | B1 | 2/2012 |
| WO | 02060407 | A1 | 8/2002 |
| WO | 03037281 | A1 | 5/2003 |
| WO | 2013190130 | A1 | 12/2013 |
| WO | 2019001940 | A1 | 1/2019 |
| WO | 2022094731 | A1 | 5/2022 |

* cited by examiner

*Primary Examiner* — Necholus Ogden, Jr.

(74) *Attorney, Agent, or Firm* — Mendelsohn Dunleavy, P.C.

(57) ABSTRACT

Premium skincare tablets that transform into unique facial cleansing products upon use. Disclosed is a cosmetic cleansing composition which includes a mixture of at least one starch, at least one flour, at least one filler, and at least three surfactants. The composition is in the form of a solid tablet, and the composition does not contain a synthetic preservative, added water or a coating on an outer surface of the solid tablet.

9 Claims, No Drawings

FACE CLEANSER BEADS

This application claims priority to U.S. provisional patent application No. 63/505,260 filed May 31, 2023, the entire contents of which are hereby incorporated by reference in their entirety.

The disclosure relates to a facial skin care cleansing product that is environmentally friendly. The disclosure also relates to a method of making and a method of using the facial skin care cleansing product.

SUMMARY OF THE INVENTION

Additional details and advantages of the disclosure will be set forth in part in the description which follows, and/or may be learned by practice of the disclosure. The details and advantages of the disclosure may be realized and attained by means of the elements and combinations particularly pointed out in the appended claims. It is to be understood that both the foregoing general description and the following detailed description are exemplary and explanatory only and are not restrictive of the disclosure, as claimed.

1. In an aspect, the present invention is drawn to a cosmetic cleansing composition comprising a mixture of:

a) At least one starch
b) at least one flour
c) at least one filler, and
d) at least three surfactants, wherein the composition is in the form of a solid tablet, and said composition does not contain a synthetic preservative, added water or a coating on an outer surface of the solid tablet.

2. The cosmetic cleansing composition of sentence 1, wherein the solid tablet can be configured to be crushable between the fingers to form a powder.
3. The cosmetic cleansing composition of sentence 2, wherein the powder can be configured to mix with water to form a lather.
4. The cosmetic cleansing composition of any one of the previous sentences, wherein each tablet can weigh 0.25 g to 2.0 g, or 0.25 g to 0.75 g, or about 0.5 g.
5. The cosmetic cleansing composition of any one of the previous sentences, wherein the starch can be at least one selected from the group consisting of Corn starch, Potato starch, Tapioca starch, Arrowroot starch, Wheat starch, Cassava starch, Sweet potato starch, Sorghum starch, Oat starch, Barley starch, Millet starch, Rice starch, Rye starch, Amaranth starch, Quinoa starch, and Buckwheat starch.
6. The cosmetic cleansing composition of any one of the previous sentences, wherein the starch can be in an amount of 40-60 wt. %, or 50-55 wt. % based on the total weight of the composition.
7. The cosmetic cleansing composition of any one of the previous sentences, wherein the starch can be at least one selected from the group consisting of Corn starch, Potato starch, and Rice starch.
8. The cosmetic cleansing composition of any one of the previous sentences, wherein the starch can be Rice starch.
9. The cosmetic cleansing composition of any one of the previous sentences, which can further comprise a vegetable oil or wax.
10. The cosmetic cleansing composition of any one of the previous sentences, wherein the vegetable oil or wax can be derived from Olive, Coconut, Canola, Castor seed, Sunflower, Soybean, Peanut, Corn, Sesame, Oat, Avocado, Flaxseed, Safflower, Grape seed, Walnut, Almond, Hempseed and mixtures thereof.
11. The cosmetic cleansing composition of any one of the previous sentences, wherein the vegetable oil or wax can be in an amount of up to 10 wt. %, or 0.05 wt. % to 5 wt. %, or 0.5 wt. % to 4 wt. % based on the total weight of the composition.
12. The cosmetic cleansing composition of any one of the previous sentences, wherein the vegetable oil or wax can be derived from at least one selected from the group consisting of Soybean, Peanut, Corn, Sesame, and Oat.
13. The cosmetic cleansing composition of any one of the previous sentences, wherein the vegetable oil or wax can be Oat oil.
14. The cosmetic cleansing composition of any one of the previous sentences, wherein the flour can be at least one selected from the group consisting of All-purpose flour, Whole wheat flour, Almond flour, Oat flour, Coconut flour, Buckwheat flour, Rice flour, Quinoa flour, Chickpea flour, Spelt flour, Barley flour, Rye flour, Amaranth flour, Millet flour, and Sorghum flour.
15. The cosmetic cleansing composition of any one of the previous sentences, wherein the flour can be in an amount of 5-20 wt. %, or 8-12 wt. % based on the total weight of the composition.
16. The cosmetic cleansing composition of any one of the previous sentences, wherein the flour can be at least one selected from the group consisting of Whole wheat flour, Oat flour, and Rice flour.
17. The cosmetic cleansing composition of any one of the previous sentences, wherein the flour can be Oat flour.
18. The cosmetic cleansing composition of any one of the previous sentences, which can further comprise at least one enzyme.
19. The cosmetic cleansing composition of any one of the previous sentences, wherein the enzyme can be selected from the group consisting of Papain, Bromelain, Lipase, Alpha-Amylase, Coenzyme Q10, Protease and mixtures thereof.
20. The cosmetic cleansing composition of any one of the previous sentences, wherein the enzyme can be in an amount of up to 10 wt. %, or 0.001 wt. % to 5 wt. %, or 0.005 wt. % to 4 wt. % based on the total weight of the composition.
21. The cosmetic cleansing composition of any one of the previous sentences, which can further comprise a natural antioxidant.
22. The cosmetic cleansing composition of any one of the previous sentences, wherein the natural antioxidant can be selected from Green Tea Extract, Grape Seed Extract, Blue butterfly pea extract, Vitamin E, Rosemary Extract, Pomegranate Extract, Turmeric Extract, Acai Berry Extract, Licorice Root Extract and mixtures thereof.
23. The cosmetic cleansing composition of any one of the previous sentences, wherein the natural antioxidant can be in an amount of up to 10 wt. %, or 0.05 wt. % to 5 wt. %, or 0.5 wt. % to 4 wt. % based on the total weight of the composition.
24. The cosmetic cleansing composition of any one of the previous sentences, wherein the natural antioxidant can be at least one selected from the group consisting of Pomegranate Extract, Turmeric Extract, Acai Berry Extract and Blue butterfly pea extract.
25. The cosmetic cleansing composition of any one of the previous sentences, wherein the filler can be at least one selected from the group consisting of silica, ceramic bead, calcium carbonate, titanium oxide, talc, magnesium silicate (particle size: about 5 microns), aluminum silicate, sand with an absolute particle size of between about 1 and 1000 microns, bentonite clay, rhassoul clay, french green clay, fuller's earth clay, dead sea clay, white cosmetic clay, kaolin clay (such as red kaolin clay, pink kaolin clay, yellow kaolin clay, and blue kaolin clay), brazilian purple clay, australian reef red clay, moroccan lava clay, and zeolite clay.

26. The cosmetic cleansing composition of any one of the previous sentences, wherein the filler can be in an amount of 0.5-20 wt. %, or 1-15 wt. %, or 1-10 wt. % based on the total weight of the composition.
27. The cosmetic cleansing composition of any one of the previous sentences, wherein the filler can be white cosmetic clay, kaolin clay, zeolite clay or mixtures thereof.
28. The cosmetic cleansing composition of any one of the previous sentences, wherein the filler can be kaolin.
29. The cosmetic cleansing composition of any one of the previous sentences, which can further comprise a fruit peel extract.
30. The cosmetic cleansing composition any one of the previous sentences, wherein the fruit peel extract can be selected from Orange Peel Extract, Lemon Peel Extract, Grapefruit Peel Extract, Lime Peel Extract, Apple Peel Extract, Pomegranate Peel Extract, Papaya Peel Extract, Strawberry Peel Extract, Blueberry Peel Extract, Pineapple Peel Extract, and mixtures thereof.
31. The cosmetic cleansing composition any one of the previous sentences, wherein the fruit peel extract can be in an amount of up to 10 wt. %, or 0.05 wt. % to 5 wt. %, or 0.1 wt. % to 4 wt. % based on the total weight of the composition.
32. The cosmetic cleansing composition of any one of the previous sentences, wherein the fruit peel extract can be at least one selected from the group consisting of Orange Peel Extract, Lemon Peel Extract, and Grapefruit Peel Extract.
33. The cosmetic cleansing composition of any one of the previous sentences, wherein the fruit peel extract can be a mixture of Orange Peel Extract and Grapefruit Peel Extract.
34. The cosmetic cleansing composition of any one of the previous sentences, which can further comprise a moisturizer.
35. The cosmetic cleansing composition of any one of the previous sentences, wherein the moisturizer can be selected from Hyaluronic Acid or derivative thereof (such as Hydrolyzed Sodium Hyaluronate, Sodium Hyaluronate Crosspolymer, Hydrolyzed Hyaluronic Acid, Sodium Acetylated Hyaluronate, Pentylene Glycol, Glycerin, Butylene Glycol, Propylene Glycol, Panthenol (provitamin B5), and mixtures thereof.
36. The cosmetic cleansing composition of any one of the previous sentences, wherein the moisturizer can be in an amount of up to 10 wt. %, or 0.05 wt. % to 5 wt. %, or 0.1 wt. % to 4 wt. % based on the total weight of the composition.
37. The cosmetic cleansing composition of any one of the previous sentences, wherein the moisturizer can be a mixture of hyaluronic acids having a trimodal molecular weight distribution.
38. The cosmetic cleansing composition of any one of the previous sentences, wherein the at least three surfactants can be selected from the group consisting of Sunfloweroyl Methylglucamide, Sodium Methyl Oleoyl Taurate, Sodium Methyl Cocoyl Taurate, Sodium Cocoyl Isethionate, Sodium Lauryl Sulfate, Sodium Lauroyl Sarcosinate, Cocamidopropyl Betaine, Sodium Laureth Sulfate, Sodium Cocoamphoacetate, Sodium Lauroamphoacetate, Sodium Trideceth Sulfate, Disodium Lauryl Sulfosuccinate, Sodium Lauroyl Methyl Isethionate, Sodium Lauroyl Glutamate, Sodium Cocoate, Sodium Oleate, Sodium Stearate, Sodium Palmitate, Coco-Glucoside, Decyl Glucoside, Lauryl Glucoside, Disodium Cocoamphodiacetate, Sodium Lauroyl Lactylate, Sodium Cocoyl Glutamate, Cocoyl Methyl Glucamide and Sodium Stearoyl Glutamate; preferably, the cosmetic cleansing composition can comprise at least 4 surfactants.
39. The cosmetic cleansing composition of any one of the previous sentences, wherein the at least three surfactants can be present in an amount of 10-50 wt. %, or 20-40 wt. %, or 25-40 wt. % based on the total weight of the composition.
40. The cosmetic cleansing composition of any one of the previous sentences, said composition can consist essentially of:

A) Rice Starch,
B) Oat Oil,
C) Oat Flour,
D) Papain,
E) Blue Butterfly Pea Extract,
F) Kaolin,
G) Grapefruit Extract,
H) Orange Peel Extract,
I) a mixture of hyaluronic acids having a trimodal molecular weight distribution, and
J) at least three surfactants.

41. In another aspect of the invention, is a process of preparing the tablet of the cosmetic cleansing composition of any one of the previous sentences, comprising granulating solid ingredients into a powder, spray drying the oily/waxy ingredients onto the powders, and then pressing a sufficient quantity with a tablet press to form the tablet.
42. In another aspect of the invention, the cosmetic cleansing composition of any one of the previous sentences is in the form of a tablet, wherein the tablet is formed in a process comprising granulating solid ingredients into a powder, spray drying the oily/waxy ingredients onto the powders, and then pressing a sufficient quantity with a tablet press to form the tablet.
43. In another aspect of the invention, is a method of cleansing comprising:

compressing the tablet of any one of the previous sentences by hand with sufficient force to crumble the tablet into a powder, while holding the powder in the palm, add water and rub hands together to mix water and powder until a lather forms, apply the lather to an area of facial skin of a human subject in need thereof to be gently cleansed.

DETAILED DESCRIPTION OF THE INVENTION

Facial Skin Care Cleansing Product Composition

The facial skin care cleansing product is a cleanser concentrate that is soft-pressed into an uncoated tablet. The uncoated tablet can break apart between a user's fingers to form a powder. By hand mixing the powder with a few drops of water, the powder will transform the cleanser concentrate into a luxurious lather. Since there is no added water in the composition, the skin care cleansing product does not require any artificial preservatives. To ensure proper dosing of the cleanser concentrate, the skin care cleansing product is in tablet form (rather than powder form). This unique product is a cleanser for the face and is comprised of ingredients which are known to have the advantages of being gentle, hydrating and mildly exfoliating.

One or more starch can be included in the cosmetic cleansing composition in view of its ability to absorb oil, control shine, minimize pore appearance, and repair and maintain the natural skin barrier. Rice starch is preferred.

One or more vegetable oil or wax can be included in the cosmetic cleansing composition in view of its nourishing and moisturizing properties. It may provide hydration, improve skin texture, and promote a smoother appearance. Vegetable oils or waxes such as ones made from the sunflower may contain essential fatty acids, such as linoleic acid, which help maintain the skin's barrier function and retain moisture. Vegetable oils or waxes containing vitamin E, such as oat oil are preferred, since vitamin E helps to soften, hydrate, and protect the skin, and may help reduce inflammation as well as boost ceramide levels in the skin which lead to intense hydration.

One or more vegetable flour can be included in the cosmetic cleansing composition in view of its ability to restore moisture to dry skin and create a protective barrier against UF rays and impurities. Vegetable flour has soothing and calming properties, particularly for sensitive or irritated skin. The fine particles make it suitable for gentle exfoliation. It can help remove dead skin cells and unclog pores, leaving the skin smoother and brighter without causing excessive irritation. Some flours, like oat flour are particularly advantageous for containing natural compounds called avenanthramides that possess anti-inflammatory properties, helping to reduce redness, itching, and irritation. Oat flour is also preferred because it contains antioxidants, including vitamin E and ferulic acid, which help to combat oxidative stress and protect the skin against free radicals. This can contribute to a reduction in the signs of aging, such as fine lines, wrinkles, and age spots.

One or more enzyme can be included in the cosmetic cleansing composition to provide benefits such as exfoliation, moisturization, and anti-aging effects. Papain is preferred and is a naturally derived enzyme from papaya that can contribute to the breakdown of protein in the skin, helping to remove damaged skin cells allowing healthy tissue to heal. It may also soothe skin irritations, inflammation, lighten blemishes and improve texture.

One or more natural antioxidants can be used in the cosmetic cleansing composition. The natural antioxidant is selected from Green Tea Extract, Grape Seed Extract, Blue butterfly pea extract, Vitamin E, Rosemary Extract, Pomegranate Extract, Turmeric Extract, Acai Berry Extract, Licorice Root Extract and mixtures thereof. Blue butterfly pea extract is preferred, since its powerful antioxidants stimulate collagen growth and aid in calming skin irritation and redness.

One or more filler can be included in the cosmetic cleansing composition to provide consistency and texture to the composition. Fillers such as kaolin provide additional advantages, such as its excellent oil-absorbing properties, making it effective in controlling excess sebum on the skin without clogging the pores. Kaolin imparts a smooth and silky texture to the cosmetic cleansing composition.

The cosmetic cleansing composition may exclude inorganic lubricants such as magnesium stearate.

One or more fruit peel extract can be included in the cosmetic cleansing composition in view of its antioxidant properties. Antioxidants help protect the skin from damage caused by free radicals, which are unstable molecules that can contribute to premature aging and skin damage. The fruit peel extract adds brightening and revitalizing effects to the cosmetic cleansing composition. Preferably, the one or more fruit peel extract is a combination of grapefruit peel extract and orange peel extract.

One or more esters of fatty acids can be used in the cosmetic cleansing composition as an emollient and skin-conditioning agent. The esters of fatty acids include Isopropyl Palmitate, Ethylhexyl Palmitate, Cetyl Palmitate, Glyceryl Stearate, Isopropyl Shea Butterate, Isopropyl Myristate, Butyl Stearate, Stearyl Palmitate, Caprylic/Capric Triglyceride, Decyl Oleate, Lauryl Lactate and mixtures thereof.

One or more moisturizer can be included in the cosmetic cleansing composition to hydrate the skin. In a preferred embodiment, the moisturizer is a blend of hyaluronic acids (HA) having a trimodal molecular weight (MW) distribution, i.e., a high molecular weight fraction, a mid-molecular weight fraction and a low molecular weight fraction. The weight fractions can be determined by GPC using a column and an aqueous solvent appropriate for molecular weights ranging from 10 kDa to 3000 kDa. The High MW HA fraction can be used to hydrate the skin, for barrier repair function, for firming, lifting, and for soothing and moisturizing dry skin. The Mid MW HA fraction can penetrate deeper into the stratum corneum and stimulates corneocyte differentiation and protection of skin's NMF (Natural Moisturizing Factor), making it the ideal ingredient to restore moisture where it is most needed and to aid against inflammation and irritation (both natural and introduced), and to heal sensitive dry, damaged skin. The Low MW HA fraction can penetrate deeper into the epidermis and upper layer of the dermis and into the narrow extracellular space between the stratified keratinocytes layers to induce production of native HA and to aid in proliferation of the keratinocytes.

At least three surfactants can be included in the cosmetic cleansing composition. The surfactants can break down and remove dirt, oil, and other impurities from the skin's surface. They have both hydrophilic (water-loving) and lipophilic (oil-loving) properties, allowing them to interact with both water and oil, thereby facilitating the removal of various types of debris from the skin. The at least three surfactants can be selected from the group consisting of Sunfloweroyl Methylglucamide, Sodium Methyl Oleoyl Taurate, Sodium Methyl Cocoyl Taurate, Sodium Cocoyl Isethionate, Sodium Lauryl Sulfate, Sodium Lauroyl Sarcosinate, Cocamidopropyl Betaine, Sodium Laureth Sulfate, Sodium Cocoamphoacetate, Sodium Lauroamphoacetate, Sodium Trideceth Sulfate, Disodium Lauryl Sulfosuccinate, Sodium Lauroyl Methyl Isethionate, Sodium Lauroyl Glutamate, Sodium Cocoate, Sodium Oleate, Sodium Stearate, Sodium Palmitate, Coco-Glucoside, Decyl Glucoside, Lauryl Glucoside, Disodium Cocoamphodiacetate, Sodium Lauroyl Lactylate, Sodium Cocoyl Glutamate, Cocoyl Methyl Glucamide and Sodium Stearoyl Glutamate. Preferably, the cosmetic cleansing composition comprises at least 4 surfactants.

The cosmetic cleansing composition of the disclosure does not contain any added water. There may be some residual moisture absorbed from the atmosphere. It is preferred for there to be less than 0.5 wt. %, or less than 0.1 wt. % or less than 0.01 wt. % or less than 0.001 wt. % water based on the total weight of the solid tablet composition.

The cosmetic cleansing composition of the disclosure does not contain a synthetic preservative, added water or a coating (or layer) on an outer surface of the solid tablet.

Process of Making the Facial Skin Care Cleansing Product

In an aspect, the disclosure relates to a process of preparing the facial skin care cleansing product composition into a tablet. The process comprises granulating solid ingredients into a powder, spray drying the oily/waxy ingredients onto the powders, and then pressing a sufficient quantity with a tablet press to form the tablet.

Method of Using the Facial Skin Care Cleansing Product

In an aspect, the disclosure relates to a method of cleansing facial skin comprising:

compressing the tablet by hand with sufficient force to crumble the tablet into a powder, while holding the powder in the palm, add water and rub hands together to mix water and powder until a lather forms, apply lather to the facial skin of a human subject in need thereof to be gently cleansed.

The foregoing embodiments are susceptible to considerable variation in practice. Accordingly, the embodiments are not intended to be limited to the specific exemplifications set forth hereinabove. Rather, the foregoing embodiments are within the spirit and scope of the appended claims, including the equivalents thereof available as a matter of law.

The patentees do not intend to dedicate any disclosed embodiments to the public, and to the extent any disclosed modifications or alterations may not literally fall within the scope of the claims, they are considered to be part hereof under the doctrine of equivalents.

It is to be understood that each component, compound, substituent or parameter disclosed herein is to be interpreted as being disclosed for use alone or in combination with one or more of each and every other component, compound, substituent or parameter disclosed herein.

As used throughout the specification and claims, "a" and/or "an" may refer to one or more than one. Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. It is intended that the specification and examples be considered as exemplary only, with a true scope and spirit of the disclosure being indicated by the following claims.

It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range.

The term "synthetic" and the term "natural" are used herein. The term "synthetic" refers to something that is artificially created or produced by human intervention. It is often used to describe substances, materials, or products that are made through chemical or manufacturing processes, rather than being naturally occurring. Synthetic items are typically engineered or synthesized to mimic or replicate natural counterparts, but they are not found in nature in their exact form. The term "natural" refers to something that exists or occurs in nature, without human intervention or artificial alterations. Natural compounds are those that are not created or modified by human beings but are part of the natural world. A natural substance can be isolated from a plant or animal but is not further chemically modified.

The present disclosure can "comprise" (open ended) or "consist essentially of" the components of the present invention as well as other ingredients or elements described herein. As used herein, "comprise", "comprises" or "comprising" is open ended and means the elements recited, or their equivalent in structure or function, plus any other element or elements which are not recited. The terms "having" and "including" are also to be construed as open ended unless the context suggests otherwise. The transitional phrase, "consists essentially of" or "consisting essentially of" is intended to limit the scope of a sentence to the specified materials or steps and those that do not materially affect the basic and novel characteristic(s) (such as cosmetic characteristics) of the claimed invention.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

The invention claimed is:

1. A cosmetic cleansing composition consisting essentially of a mixture of:

a) rice starch
b) oat Flour flour
c) Kaolin
d) Papain,
E) Oat Oil,
F) Blue Butterfly Pea Extract,
G) Grapefruit Extract,
H) Orange Peel Extract,
I) a mixture of hyaluronic acids having a trimodal molecular weight distribution, and
J) at least three surfactants, wherein the composition is in the form of a solid tablet, and said composition does not contain a synthetic preservative, added water or a coating on an outer surface of the solid tablet.

2. The cosmetic cleansing composition of claim 1, wherein the solid tablet is configured to be crushable between the fingers to form a powder.

3. The cosmetic cleansing composition of claim 2, wherein the powder is configured to mix with water to form a lather.

4. The cosmetic cleansing composition of claim 1, wherein each tablet weighs 0.25 g to 2.0 g.

5. The cosmetic cleansing composition of claim 1, wherein the starch is in an amount of 40-60 wt. % based on the total weight of the composition.

6. The cosmetic cleansing composition of claim 1, wherein the vegetable oil or wax is in an amount of up to 10 wt. %, based on the total weight of the composition.

7. The cosmetic cleansing composition of claim 1, wherein the flour is in an amount of 5-20 wt. % based on the total weight of the composition.

8. The cosmetic cleansing composition of claim 1 which is in the form of a tablet, wherein the tablet is formed in a process comprising granulating solid ingredients into a powder, spray drying the oily/waxy ingredients onto the powders, and then pressing a quantity with a tablet press to form the tablet.

9. A method of cleansing comprising:

compressing the tablet of claim 8 by hand with sufficient force to crumble the tablet into a powder, while holding the powder in the palm, add water and rub hands together to mix water and powder until a lather forms, apply the lather to an area of facial skin of a human subject in need thereof to be gently cleansed.

* * * * *